United States Patent [19]

Pike

[11] Patent Number: 5,121,536

[45] Date of Patent: Jun. 16, 1992

[54] METHOD FOR MAKING PRESTRESSED COLUMN

[75] Inventor: Kelly A. Pike, Laguna Hills, Calif.

[73] Assignee: Applied Vascular Devices, Inc., Laguna Hills, Calif.

[21] Appl. No.: 643,525

[22] Filed: Jan. 18, 1991

[51] Int. Cl.⁵ .................... B21D 39/00; B23P 11/00
[52] U.S. Cl. ...................... 29/447; 29/448; 29/450; 29/508; 29/517
[58] Field of Search ............... 29/447, 450, 448, 508, 29/515, 516, 517

[56] References Cited

U.S. PATENT DOCUMENTS

| | | |
|---|---|---|
| 2,641,302 | 6/1953 | Martin . |
| 2,766,806 | 8/1954 | Rothermel . |
| 2,783,819 | 3/1957 | Duff . |
| 2,797,730 | 7/1957 | Martin . |
| 3,290,196 | 12/1966 | Duff . |
| 3,779,846 | 12/1973 | Kleykamp . |
| 3,811,178 | 5/1974 | Tarnavsky et al. ............. 29/517 |
| 3,982,982 | 9/1976 | Chudgar . |
| 4,477,147 | 10/1984 | Winter et al. ............. 29/517 X |

Primary Examiner—Timothy V. Eley
Attorney, Agent, or Firm—Richard L. Myers

[57] ABSTRACT

A catheter includes a spring having a plurality of convolutions disposed along a longitudinal axis, and a first modulus. A sheath overlying the spring engages the convolutions of the spring and imparts to the spring axial compressive stresses which increase the modulus of the spring. The catheter can be manufactured by inserting the spring into a tube of Hytrel ® material, stretching the tube at a transition region which advances along thhe tube causing the tube to neck down onto the spring. The stretching develops internal stresses which are utimately imparted to the spring thereby increasing the modulus of the catheter.

26 Claims, 3 Drawing Sheets

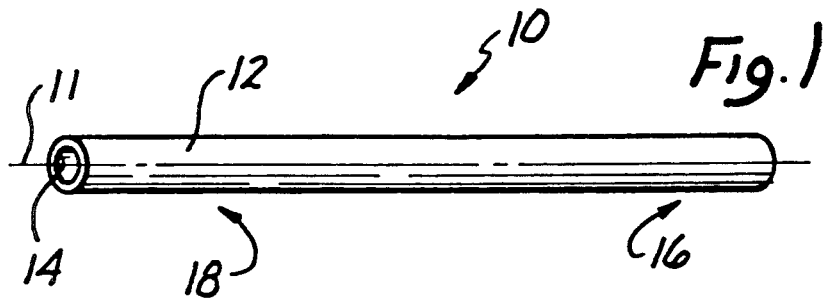
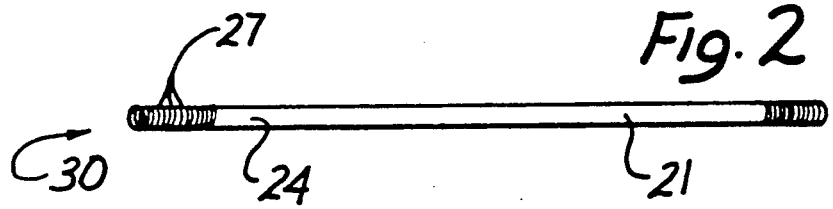
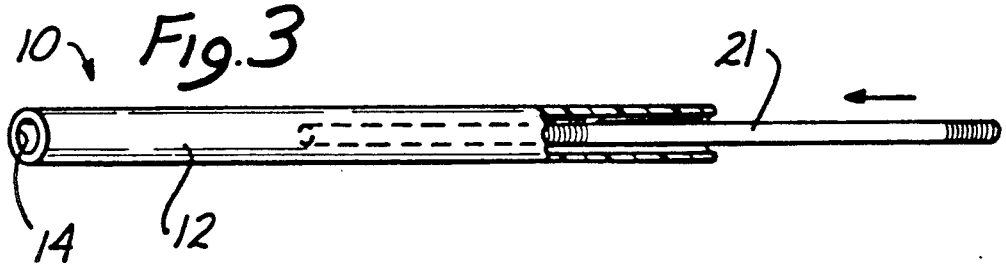
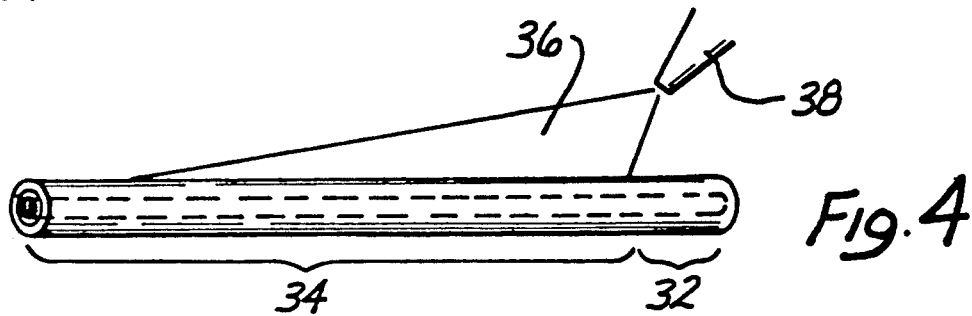
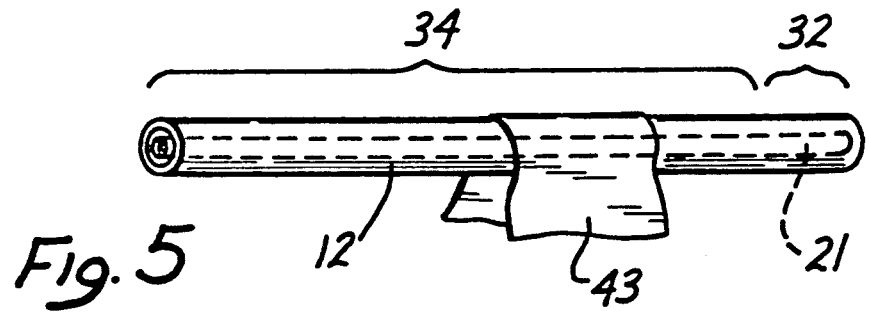
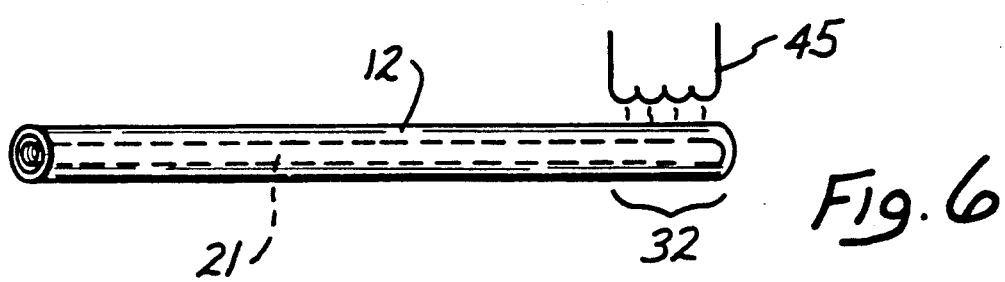

METHOD FOR MAKING PRESTRESSED COLUMN

BACKGROUND OF THE INVENTION

1. Field of the Invention

This invention relates generally to methods and apparatus for strengthening columns or elongate tubes, and more specifically for strengthening spring reinforced catheters and other surgical access devices.

2. Discussion of the Prior Art

It is often desirable to increase the strength of elongate columns or tubes, such as tubes formed from flexible plastics. Ordinarily one would increase the wall thickness of the tube in order to provide increased strength, but in some cases there are limitations on the maximum diameter which can be tolerated. Such is the case with medical catheters which require the smallest possible outer diameter.

For such catheters, it has been found desirable to form the plastic tube over a spring thereby increasing the column strength of the catheter without sacrificing either flexibility or size. The modulus of such a combination has exceeded the sum of moduli associated with the spring and the tubing.

Spring reinforced catheters have been made from several processes all of which require the application of externally generated heat. Most commonly, the spring has been inserted into the bore of flexible polyvinylchloride tubing which is then heat shrunk so that it collapses onto the spring. This is a complex process and somewhat restricted as to the materials which can be used for the tubing.

Coextrusion has also been used to manufacture spring reinforced catheters. In this process, the spring is deployed through an extruder as the molten plastic is formed around the spring. Molding processes have also been used for relatively short lengths of tubing.

In all of these methods of manufacture, heat must be applied to the tubing in significant quantities in order to effectively melt or otherwise shrink the tubing onto the spring. In its melted state, the tubing forms a sheath over the spring which is essentially free of stress due to the applied heat. This results from the fact that any stresses in the tubing are essentially relieved by the heat. The resulting structure has a relatively low modulus. Each of these methods of manufacture requires complex machinery for coextrusion, heat shrinking or molding; in addition, the related processes are extensive and must be carefully controlled.

Particularly in a catheter construction, the tubing must meet several requirements. For the processes of the prior art, it is desirable that the material be shrinkable or at least heat formable. It is desirable that it have a high tensile strength and good flexibility. Complex catheters, requiring balloons or thermistors or other associated structures, also require that the tubing material be solvent bondable.

Polyvinylchloride, polyethylene, urethanes and nylon can all be heat shrunk, but each of these materials fail to meet one or more of the forgoing criteria.

SUMMARY OF THE INVENTION

These shortcomings of the prior art are overcome in the present invention by a new process for forming spring reinforced tubing and a material particularly adapted to this process and the requirements for catheter construction.

"Hytrel ®" is a trademark of E. I. duPont de Nemours & Co. and is applied to a material which is solvent bondable, flexible, heat formable, and has a high tensile strength. Although this material is not particularly heat shrinkable, it can be longitudinally stretched at normal room temperatures without the application of significant heat. By merely fixing one end of a tube of Hytrel ® and grasping the other end of the tube, a tensile stress can be applied to the material which will cause the tube to neck-down, thinning the walls of the tube and decreasing the internal diameter of the bore. This transformation occurs at a zone of transition which progresses along the tube as it is stretched. This process will be referred to herein as "cold extrusion."

It is of particular significance that the stretching of the tubing imparts internal stresses which cause the tubing to shrink slightly thereby imparting the stresses to the internal spring. This results in a substantial increase in the column strength of the catheter, an increase which can be measured in the modulus of the combination.

One aspect of the invention includes a method for making a spring reinforced catheter including the steps of providing an elongate tube defined by a proximal end and a distal end, the tube having an interior bore with an inside diameter; providing a spring having a proximal end, a distal end, and an outside diameter less than the inside diameter of the bore of the tube; inserting the spring at least partially into the bore of the tube; marginally increasing the temperature of the tube at a particular location along the tube relative to the temperature of the remainder of the tube; and stretching the tube at the particular location to reduce the diameter of the interior bore of the tube.

In another aspect of the invention, the method includes the steps of increasing the temperature of the tube at a particular location, drawing the walls of the tube onto the spring at the particular location and exothermically heating the tube at progressive locations along the remainder of the tube.

In still a further aspect of the invention the method includes the steps of stretching the tube to draw the walls of the tube radially inwardly into heat transferring contact with the spring and heating the tube at positions progressing axially from the particular location.

The resulting spring reinforced catheter includes a spring having a longitudinal configuration and a first modulus in its unreinforced state, a sheath overlying the spring and axially compressing the spring to a second state wherein the spring has second modulus greater than the first modulus.

These and other features and advantages of the invention will be more apparent with a description of preferred embodiments and reference to the associated drawings.

DESCRIPTION OF THE DRAWINGS

FIG. 1 is a side-elevation view of a cold extrudable tube;

FIG. 2 is a side-elevation view of an unreinforced spring;

FIG. 3 is a side-elevation view illustrating the process step of inserting the spring into the tube in a preferred method of the invention;

FIG. 4 is a side-elevation view of a process step whereby a portion of the tube is cooled with a sprayed fluid;

FIG. 5 is a side-elevation view illustrating a step of wiping the tube with an evaporative agent;

FIG. 6 is a side-elevation view illustrating the step of heating a portion of the tubing;

DESCRIPTION OF PREFERRED EMBODIMENTS

Figure 7:
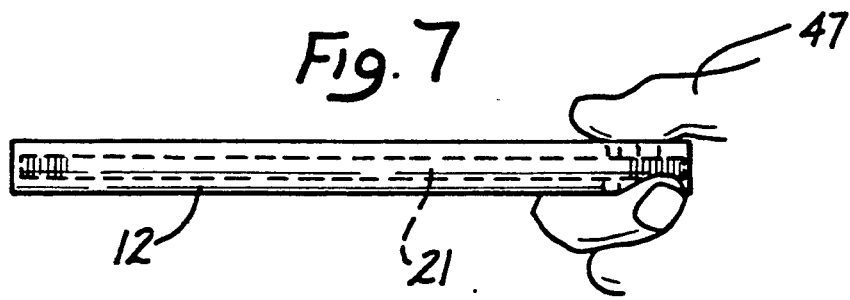
FIG. 7 is a side-elevation view illustrating the step of grasping one end of the tubing and heating the tubing where it is grasped.

A tube is illustrated in FIG. 1 and designated generally by the reference numeral 10. The tube 10 can have substantially any dimension but for most purposes will have a high aspect ratio such that its length is substantially greater than its cross-sectional dimension. The tube 10 will typically be cylindrical about an axis 11 and will include walls 12 extending radially between an outside diameter and an inside diameter of the tube 10. The walls 12 define an inner bore 14 which extends axially between a distal end 16 and a proximal end 18 of the tube 10.

In accordance with a preferred method and embodiment of the invention, the tube 10 is formed from a material which can be cold extruded. That is, the ends 16 and 18 of the tube can be separated at room temperature stretching the tube along the axis 11. During the stretching the walls 12 of the tube 10 neck down decreasing both the inside diameter and outside diameter of the tube. It follows that both the thickness of the walls 12 and the diameter of the bore 14 are decreased in this process of cold extrusion.

A spring is illustrated generally in FIG. 2 and designated by the reference numeral 21. The spring 21 is formed from a wire 24 typically having a circular cross-section and being wound into spring convolutions 27 adjacent pairs of which may be contacting. The convolutions 27 provide the spring 21 with an outside diameter less than the diameter of the tube 10, as well as an inside diameter which characterizes a hollow passage 30 extending axially of the spring 21. The wire 24 will typically be formed from stainless steel and will have a cross-sectional diameter of 0.005 inches. In a preferred method involving catheter construction, the tube has an outside diameter of 0.039 inches, and an inside diameter of 0.018 inches; the spring 21 is characterized by an outside diameter of 0.016 inches and an inside diameter of 0.006 inches.

Materials which can be cold extruded include nylon; however, this material is generally unsuitable for complex catheter construction because it is not solvent bondable. A preferred material is manufactured by DuPont and sold under the trademark "HYTREL ®". This material is not only cold extrudable but also solvent bondable. It provides a high tensile strength and flexibility which is particularly appreciated in catheter construction. It is also heat deformable. The more common materials found in the art of catheter construction, namely polyvinylchloride, polyethylene and urethanes, are not particularly susceptible to cold extrusion and therefore do not benefit as much from the present concept.

In a preferred method of manufacture, the tube 10 is axially stretched causing the tube to neck down initially at the point of greatest weakness. This point will usually be at a particular location along the tube 10 where the temperature is the highest. In this region the tube 10 will first yield to the stresses associated with stretching.

While the process could proceed without regard to the initial position of that transition region, it may be desirable to dictate that position by initially locating the transition region at a preferred position such as the proximal end 16 of the tube 10. In FIG. 4 this particular location is designated generally by a bracket 32. It is desirable that the temperature of the tube 10 at this particular location 32 be relatively greater than the temperature of the remainder of the tube 10 which is designated by the bracket 34.

One way of relatively heating the particular location 32 is to cool the remainder 34 of the tube 10. This can be accomplished by spraying the remainder 34 with cold air 36 from a nozzle 38 as illustrated in FIG. 4. Another way of cooling the remainder 34 of the tube 10 is to wipe the tube in &.hat region with an evaporative agent 41, such as alcohol, using a cloth 43 or other absorbent material. This wiping step is illustrated in FIG. 5. Neither the air 36 illustrated in FIG. 4 nor the evaporative agent 41 illustrated in FIG. 5 is intended to contact the particular location 32. By thus cooling the remainder 34 of the tube 10, the particular location 32 is relatively heated making this region 32 most susceptible to deformation by stretching.

Another way of relatively heating the particular location 32 is to provide an external heat source such as a current heated wire 45 illustrated in FIG. 6. In this case the heat is applied directly to the particular location 32 and intentionally omitted from the remainder 34 of the tube 10.

In a preferred method and apparatus associated with the present invention, the tube 10 is formed of Hytrel ® material which does not require a significant temperature differential between the particular location 32 and the remainder 34 of the catheter 10. In fact, if the remainder 34 is maintained at room temperature, the particular location 32 can be sufficiently heated by merely grasping the tube 10 between the thumb and index finger of a hand 47. This will impart body heat to the particular location 32 without raising the temperature of the remainder region 34. With this process, as illustrated in FIG. 7, the temperature of the particular location 32 approaches skin temperature of the hand 47.

If it is desirable to relatively heat the particular location 32 ... which is the same as relatively cooling the remainder region 34 ... some differential in temperature must be achieved. If room temperature is substantially the same as skin temperature, about 98.6° F., the process illustrated in FIG. 7 will not be as effective as the cooling processes illustrated in FIGS. 4 and 5 or the heating process illustrated in FIG. 6. It has been found that when the room temperature is less than 87° F., a suitable temperature differential can be established with body heat as illustrated in FIG. 7.

Figure 8:
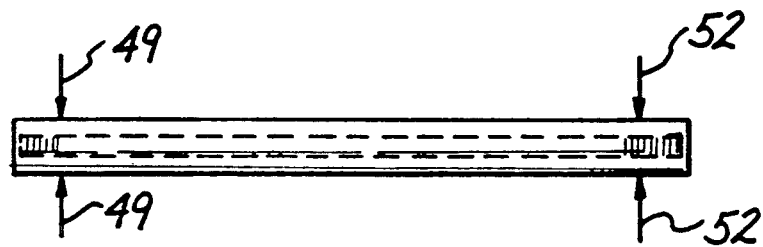
FIG. 8 is a side-elevation view illustrating the step of grasping the tubing at the respective ends of the tubing.

In axially stretching the tube 10, it is desirable that the ends 16 and 18 of the tube 10 be held in a device or other holding apparatus illustrated by the arrows 49 and 52 in FIG. 8. These holding apparatus 49 and 52 can then be separated to stretch the tube 10. For example, the holding apparatus 49 can be maintained in the fixed location and the holding apparatus 52 moved axially away from the apparatus 49 as illustrated by a pair of arrows 54.

Figure 9:
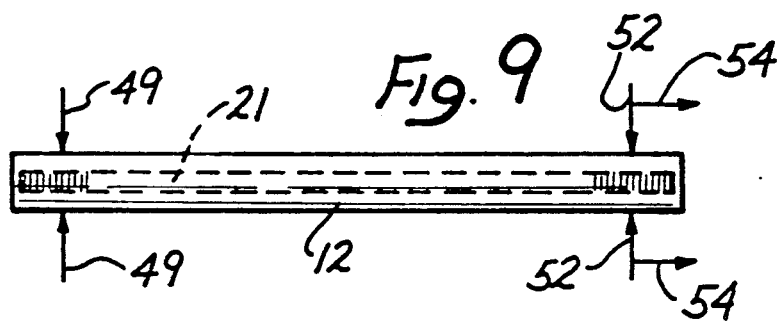
FIG. 9 is a side-elevation view illustrating the step of stretching the tubing with the spring at least partially disposed in the bore of the tubing.

FIG. 9 also illustrates another advantage associated with the preferred method. If the spring 21 is merely inserted into the bore 14 and the ends 16, 18 of the tube 10 are separated, one will not necessarily know where the spring 21 ends up in the tube. However, if the spring 21 is grasped or otherwise held along with the end 16 of the tube, its location will always be determinable in the final product.

Figure 10:
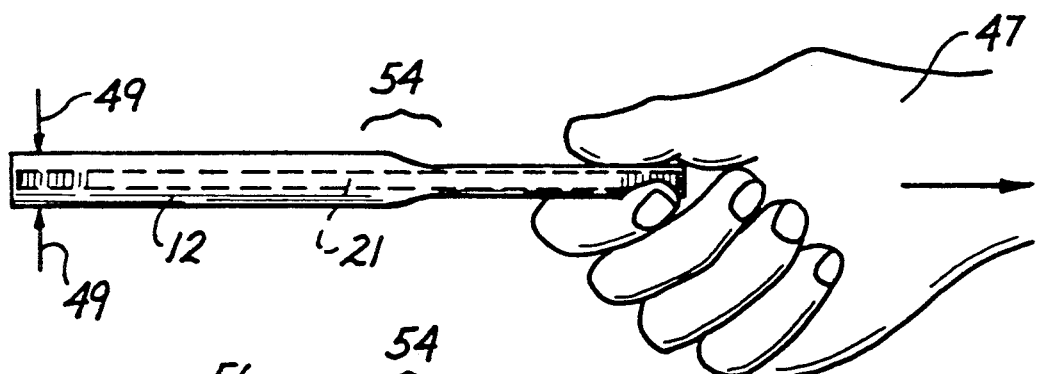
FIG. 10 is a side-elevation view illustrating the step of stretching the tubing using a hand thereby causing the tubing to neck-down onto the spring.

Thus as illustrated in FIG. 10, the hand 47 provides the means for grasping the distal end 16 of the tube 10, means for heating the distal end of the tube 10, as well as means for retaining the spring 21 in a predetermined location along the tube 10.

Figure 11:
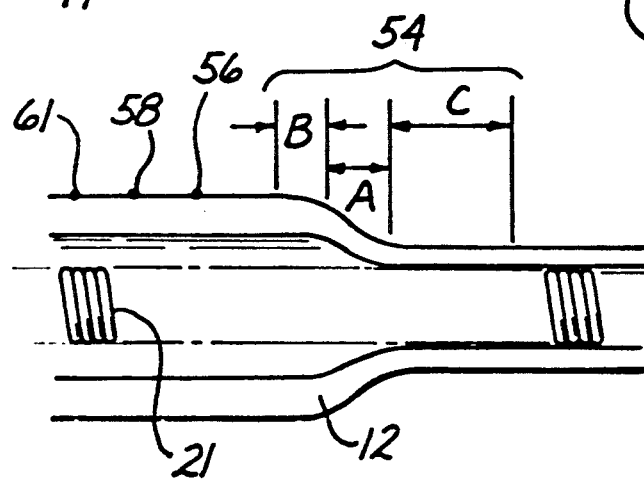
FIG. 11 is a side-elevation view illustrating a transition region which progresses along the tubing in a preferred process of the invention.
Figure 12:
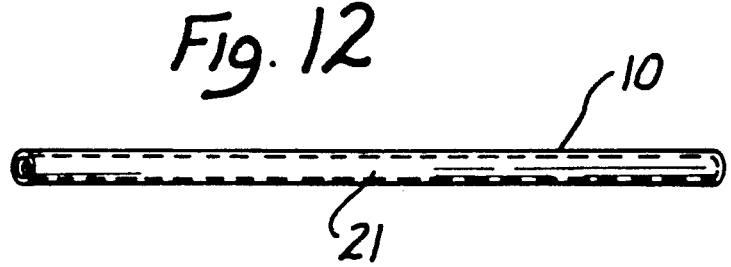
FIG. 12 is a side-elevation view illustrating the internal stresses of the tubing which axially compress the spring.
Figure 14:
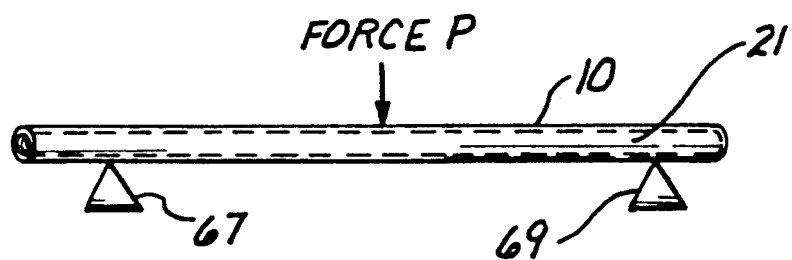
FIG. 14 illustrates apparatus for testing the modulus of a spring reinforced catheter.

As the tube 10 is stretched, it begins to deform in a relatively short transition region 54. An enlarged view of this region is presented in FIG. 11 where the region 54 is illustrated to include a first zone A, a second zone B, and a third zone C. The first zone A is characterized by the walls of the tube 12 having a temperature (such as room temperature) and being spaced from the spring. The second zone B is characterized by the tube walls 12 having a second temperature (which may be slightly higher than room temperature) and being in substantial contact with the spring 21. The zone C is disposed between zone A and zone B. In zone C, the tube walls 12 are characterized by a third temperature greater than either the first temperature associated with zone A or the second temperature associated with zone B. The diameter of the walls 12 in zone C is less than the diameter of the walls in zone A but greater than the diameter of the walls in zone B.

Zone B is disposed from zone A in a particular direction such as the distal direction of the tube 10. When the tube 10 is drawn axially as illustrated in FIG. 10, the transition zone 54 initially starts in the particular location 32 and then moves proximally along the tube 10 until the entire spring 21 is disposed in zone B.

The temperatures of the respective zones A, B, and C are particularly critical to an understanding of the cold extrusion process. As the tube 10 is initially heated in the particular location 32, the tube first deforms in this area as the enlarged tube of zone A transitions through zone C into contact with the spring 21 in zone B.

As a result of this initial physical deformation, work occurs in an exothermic reaction which heats areas of the tube adjacent to the particular location 32. This heat which occurs primarily in zone C is given up to the spring 21 when the walls 12 contact the spring in zone B. It follows that the temperature of the walls in zone B will be slightly higher than the room temperature associated with the spring 21. Continued axial tension on the tube 10 will deform the tube at the next point of weakness which will be in the area of the tube which has been heated by the mechanical exothermic reaction but has not yet passed that heat to the spring 21. This occurs in the zones A and C of the transition region 45.

If the tube 10 is grasped at the distal end 16 and drawn distally, a series of points 56, 58 and 61 disposed proximally along the tube 10 will individually and progressively pass through the zones A, C and B (in that order) as the transition region 54 moves proximally along the tube 10.

In a preferred method of manufacture, the Hytrel ® tubing is loaded at temperatures below 100° F. and cold extruded or drawn at a rate of about 1/10 inch per second. This cold extrusion tends to elongate the tube 10 by a factor of three to four while reducing the inside diameter of the tube 10 by a factor of about two.

When the tensile stretching force is stopped, the cold extruded tubing 10 tends to relax by as much as 1% to 5% of its length. This commonly occurs when tension is applied to any material, as the stretching tends to develop internal stresses which attempt to draw the material back to its original configuration when the tension is relieved. These internal stresses are of particular importance to the preferred methods and embodiments of the invention. It is these internal stresses which urge the tube 10 to shorten its length. Were it not for the presence of the spring 21 and the intimate contact between the walls 12 and the convolutions 27 of the spring 21, the tube 10 would actually exhibit a shortened axial dimension.

In a preferred method wherein the adjacent convolutions 27 of the spring 21 are initially contacting, the spring 21 cannot be further compressed, so the internal stresses of the tube 10 are actually transferred to the spring 21 thereby increasing the column strength or modulus of the spring.

Figure 13:
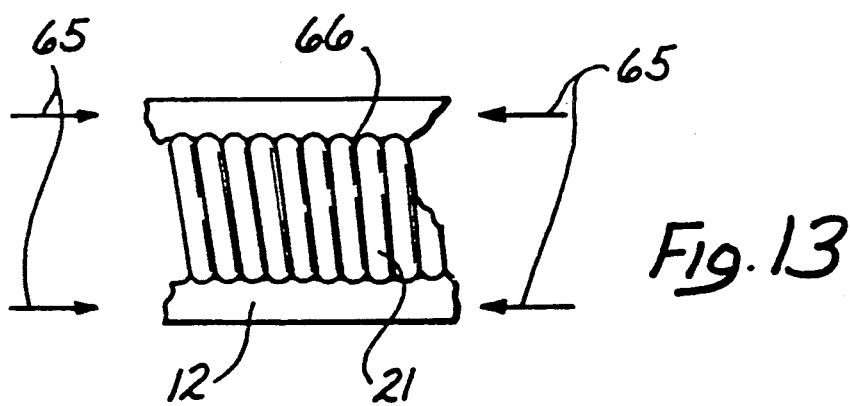
FIG. 13 is an enlarged view of the axially compressed spring of FIG. 12.
Figure 15:
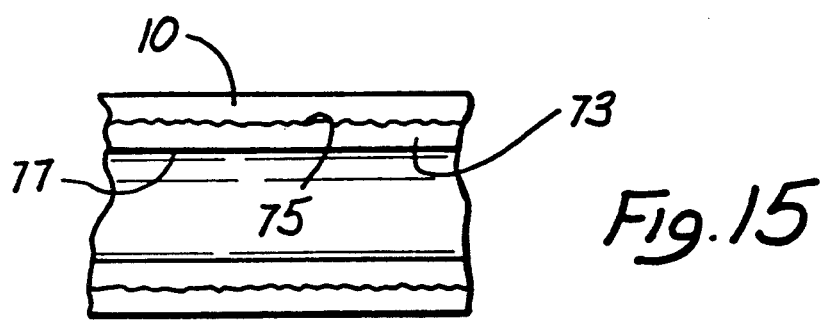
FIG. 15 is a side elevation view of an exterior tube cold extruded over an interior tube.

In the enlarged view of FIG. 13, the internal stresses are represented by arrows 65. These stresses are communicated through the walls 12 which may form a slight ridge 66 between each adjacent pair of the convolutions 27. These ridges 66 tend to press against the adjacent convolutions 27 thereby imparting the internal stresses to the spring 21.

The internal stresses offer a significant advantage to the present invention as can be appreciated with reference to FIG. 13 which illustrates a typical test for column strength or modulus. An elongate column such as the reinforced spring 21, is laid across two supports 67 and 69, and a force P is applied to the object intermediate the supports 67 and 69. The amount of deflection which results from the force P provides an indication as to the modulus or stiffness of the object. This modulus considers not only the magnitude of the force P and the distance separating the supports 67, 69, but also the cross-sectional area of the object.

The modulus of elasticity for a tube is given by the following Formula I:

$$E = \frac{PL^3}{2f(.049)(D^4 - d^4)}$$

where
L is the length between the supports 67, 69;
f is the deflection of the tube; and
P is the force applied to the tube intermediate the supports 67, 69.

Using this formula to calculate the modulus for a 2 Fr. catheter formed of Hytrel ® cold extruded over a stainless steel spring, the combination having an outside diameter of 0.027 inches and an inside diameter of 0.008 inches, indicates that the modulus of elasticity for this combination is 1,240,000 psi. In order to appreciate the significance of this figure one would have to test the catheters of the prior art using the same formula. Such a test has indicated that polyethylene tubing heat shrunk over the same spring produces a 2 Fr. catheter having a modulus of only 573,000 psi. Thus the cold extrusion process provides a modulus which is more than twice as high as that associated with the catheters of the prior art. This of course translates into axial stiffness, as well as better pushability and torquability for the catheter.

If one were to calculate the modulus of the unreinforced tube 10, and the modulus of the unreinforced spring 21, the prior art which combines these two elements would show a modulus which is perhaps 400% greater than the sum of the moduli associated with these two components. Thus even the shrink tubing or coextrusion methods of the prior art provide some increase in strength for the reinforced column. However, with the cold extrusion concept of the present invention, the modulus can be increased by as much as 800% in order to provide a desired stiffness without sacrificing the increased size of the catheter. Catheters embodying this concept and having a diameter of only 2 Fr. have exhibited a modulus greater than 1,000,000 psi.

It will be appreciated that the spring 21 is merely a preferred embodiment of a cylindrical core element that can be prestressed by the cold extrusion of an outer tube 10. In the case of the spring 21, the convolutions 27 provide a corrugated outer surface which tends to increase the coefficient of friction between the tube 10 and the spring 21. This coefficient of friction can be important in order that the axially compressing tube 10 does not slip on the spring 21 but rather engages the spring 21 to axially stress this cylindrical core element.

In a more generic embodiment, this cylindrical core element comprises a second tube 73 disposed in the bore of the outer sheath or tube 10. An irregular outer surface 75 can be provided to increase the coefficient of friction between the tube 10 and the element 73. Typically the core element 73 will have a modulus greater than the tube 10 in order to provide maximum stiffness. For example, the core element 73 may be formed of polytetrafluoroethylene and provided with a tubular configuration. This embodiment will be of particular advantage where the catheter requires a smooth inner surface 77.

Although specific preferred embodiments of the concept have been disclosed, it will be apparent that both the methods and embodiments of the invention can be otherwise characterized. Other materials may be applicable to the cold extrusion process and facilitate the formation of reinforced springs without expensive heat shrink or coextrusion machinery. Other methods for heating and cooling particular regions of the tube 10 will also be apparent to those skilled in the art. For these reasons, the scope of the invention should not be ascertained with reference only to the drawings or even the particular embodiments described, but should be determined only with reference to the following claims.

I claim:

1. A method for making a reinforced catheter comprising the following steps:

providing a tube defined by a first end and a second end, the tube having an interior bore with an inside diameter;

providing a core element having a proximal end, a distal end and an outside diameter less than the inside diameter of the bore of the tube;

inserting the core element at least partially into the bore of the tube;

increasing the temperature of the tube at a particular location along the tube relative to the temperature of the remainder of the tube; and stretching the tube at the particular location to reduce the diameter of the interior bore of the tube to a diameter substantially equivalent to the outside diameter of the core element.

2. The method recited in claim 1 wherein the increasing step includes the step of maintaining the remainder of the tube at room temperature.

3. The method recited in claim 1 wherein the increasing step includes the step of heating the tube at the particular location.

4. The method recited in claim 3 wherein during the heating step, the tube is heated to a temperature greater than the room temperature and less than about normal body temperature.

5. The method recited in claim 1 wherein the increasing step includes the step of cooling the remainder of the tube.

6. The method recited in claim 1 wherein the stretching step includes the steps of:

engaging the first end of the tube with a first holder;
engaging the second end of the tube with a second holder; and
after the engaging steps, separating the first holder from the second holder to stretch the tube.

7. The method recited in claim 6 wherein at least one of the engaging steps includes the step of grasping the tube.

8. The method recited in claim 7 wherein the one engaging step includes the step of grasping the tube at the particular location.

9. The method recited in claim 1 wherein the stretching step includes the steps of:

cooling the tube at the particular location;
exothermically heating the tube at a second location adjacent the particular location.

10. The method recited in claim 1 wherein the core element is a spring.

11. A method for reinforcing a tube extending between a first end and a second end, and having walls disposed along a longitudinal axis which define an internal bore with an inside diameter, the method including the steps of:

inserting into the bore of the tube a core element having an outside diameter less than the inside diameter of the tube;

increasing the temperature of the tube at a particular location along the tube relative to the temperature of the remainder of the tube;

drawing the walls of the tube onto the core element at the particular location;

heating the tube at progressive locations along the remainder of the tube; and cooling the tube at the progressive locations along the tube.

12. The method recited in claim 11 wherein the increasing step includes the steps of:

grasping the tube at the particular location; and heating the tube at the particular location to a temperature less than about normal body temperature.

13. The method recited in claim 11 wherein the heating step includes the step of exothermically heating the tube at the progressive locations along the tube.

14. The method recited in claim 12 wherein the grasping step includes the step of grasping the tube and the core element at the particular location.

15. The method recited in claim 11 wherein the cooling step includes the step of moving the walls of the tube into contact with the core element to withdraw heat from the tube.

16. The method recited in claim 11 wherein the core element is a spring.

17. A method for reinforcing a tube, the tube having walls disposed along a longitudinal axis and defining an internal bore with an inside diameter, the method including the steps of:
 inserting into the bore of the tube a core element having an outside diameter less than the inside diameter of the tube;
 increasing the temperature of the tube at a particular location along the tube relative to the temperature of the remainder of the tube;
 stretching the tube to draw the walls of the tube radially inwardly into heat transferring contact with the core element; and
 heating the walls of the tube at positions progressing axially from the particular location.

18. The method recited in claim 17 wherein the tube is defined by a first end and a second end, and the increasing step includes the step of increasing the temperature of the tube at one of the first end and the second end relative to the temperature of the remainder of the tube.

19. The method recited in claim 17 wherein the heating step occurs simultaneously with the stretching step, and the continued stretching of the tube draws the walls of the tube at the positions progressive inwardly into heat transferring contact with the core element.

20. The method recited in claim 17 wherein the core element is a spring.

21. A method for reinforcing a tube, the tube having a longitudinal axis and an internal bore with an inside diameter, the tube defined by a first end and a second end, the method including the steps of:
 inserting into the bore of the tube a core element having an outside diameter less than the inside diameter of the tube;
 heating the tube in a transition region including a first zone characterized by tube walls having a first inside diameter greater than the outside diameter of the core element, and a first temperature, a second zone disposed in a particular direction from the first zone, the second zone characterized by tube walls having a second inside diameter substantially equivalent to the outside diameter of the core element and a second temperature, and a third zone disposed between the first zone and the second zone, the third zone characterized by tube walls having a third inside diameter less than the first diameter and greater than the second diameter and a third temperature greater than the first temperature and the second temperature; and
 causing the transition region to move progressively axially along the tube.

22. The method recited in claim 21 wherein the causing step includes the step of causing the transition region to move progressively axially along the tube in a direction generally opposite to the particular direction.

23. The method recited in claim 21 wherein the core element is a spring.

24. A method for increasing the modulus of a column including tubular walls defining a longitudinal bore and a core element disposed in the bore, the method including the steps of:
 engaging the walls of the column;
 internally stressing the walls of the column;
 moving the stressed walls of the column into contact with the core element;
 releasing the walls of the column; and
 imparting to the core element at least some of the internal stresses of the walls of the column.

25. The method recited in claim 24 wherein during the imparting step the core element is stressed axially to impart tensile stresses to the core element of the column.

26. The method recited in claim 24 wherein the core element is a spring.

* * * * *

UNITED STATES PATENT AND TRADEMARK OFFICE
CERTIFICATE OF CORRECTION

PATENT NO. : 5,121,536
DATED : June 16, 1992
INVENTOR(S) : Kelly A. Pike

It is certified that error appears in the above—identified patent and that said Letters Patent is hereby corrected as shown below:

Col. 4, line 38 after the word "in" delete the word "&.hat" and add the word -- that --.

In the abstract, line 9 after the word "along" delete the word "thhe" and add the word -- the --.

Signed and Sealed this

Twenty-fifth Day of October, 1994

Attest:

BRUCE LEHMAN

*Attesting Officer*     *Commissioner of Patents and Trademarks*